United States Patent

Vertommen et al.

(10) Patent No.: US 10,016,369 B2
(45) Date of Patent: Jul. 10, 2018

(54) STABLE DOSAGE FORM ARTICLES FOR ORAL ADMINISTRATION

(71) Applicant: Capsugel Belgium NV, Bornem (BE)

(72) Inventors: Jan Emiel Godelieve Vertommen, Grimbergen (BE); Céline Casi, Brunstatt (FR); Annabel Igonin, Lyons (FR); Claire Geneviève Odile Tardy, Urschenheim (FR)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 15/313,074

(22) PCT Filed: May 14, 2015

(86) PCT No.: PCT/IB2015/053569
§ 371 (c)(1),
(2) Date: Nov. 21, 2016

(87) PCT Pub. No.: WO2015/186013
PCT Pub. Date: Dec. 10, 2015

(65) Prior Publication Data

US 2017/0095426 A1    Apr. 6, 2017

Related U.S. Application Data

(60) Provisional application No. 62/007,741, filed on Jun. 4, 2014.

(51) Int. Cl.
*A61K 9/48* (2006.01)
*A61K 35/612* (2015.01)
*A61K 9/00* (2006.01)

(52) U.S. Cl.
CPC .......... *A61K 9/4825* (2013.01); *A61K 9/0053* (2013.01); *A61K 9/4866* (2013.01); *A61K 9/4875* (2013.01); *A61K 35/612* (2013.01)

(58) Field of Classification Search
None
See application file for complete search history.

(56) References Cited

U.S. PATENT DOCUMENTS 4,369,069 A    1/1983    Graesser et al.
4,655,840 A    4/1987    Wittwer et al.
(Continued)

FOREIGN PATENT DOCUMENTS

JP    2006/188498        7/2006
JP    2010/260812 A    11/2010
WO    WO-2013/136183    9/2013

OTHER PUBLICATIONS

Draget, "Oligomers as Rheological Modulators in Structured Biopolymers Systems," Annual transactions of the Nordic Rheology Society, vol. 21, 2013, pp. 219-222. (Year: 2013).*

(Continued)

*Primary Examiner* — Ernst V Arnold
*Assistant Examiner* — Kyung S Chang
(74) *Attorney, Agent, or Firm* — Klarquist Sparkman, LLP

(57) ABSTRACT

A novel gelatin comprising dosage form article for oral administration and for containing therein a fill composition, the fill composition comprising one or more active materials capable of reacting with gelatin, and optionally one or more excipient materials, wherein the dosage form is made of a gelatin material and one or more plasticizers, the gelatin material having a mean molecular weight of less than about 130,000 g/mol and a low microgel content, wherein the fraction of microgel is of less than about 10% of the total number of gelatin chains of the gelatin material.

9 Claims, 3 Drawing Sheets

(56) References Cited

U.S. PATENT DOCUMENTS

2006/0269987 A1 11/2006 Dolphin et al.
2011/0045067 A1 2/2011 Haug et al.
2013/0209544 A1 8/2013 Zhang et al.

OTHER PUBLICATIONS

Babel et al., "Effect of Limed Hide Gelatine Grade on Soft Capsule Release Performance," Aug. 2013, 1 page. Retrieved from the internet: http://abstracts.aaps.org/Verify/aaps2013/postersubmissions/M1166.pdf.
"Gelita RXL: Reduced Cross-Linking Gelatine: Improving capsule shelf life and stability." Gelita RXL brochure, May 2013, 4 pages. Retrieved from the internet: http://www.gelita.com/sites/default/files/BroschüreRXLengl.0513.pdf.
International Search Report and Written Opinion, dated Aug. 17, 2015, issued in corresponding International Application No. PCT/IB2015/053569, 14 pages.

\* cited by examiner

STABLE DOSAGE FORM ARTICLES FOR ORAL ADMINISTRATION

CROSS REFERENCE TO RELATED APPLICATIONS

This is the U.S. National Stage of International Application No. PCT/IB2015/053569, filed May 14, 2015, which was published in English under PCT Article 21(2), which in turn claims the benefit of U.S. Provisional Application No. 62/007,741, filed Jun. 4, 2014, each of which is incorporated herein in its entirety.

FIELD

The present disclosure relates to a novel stable dosage form, preferably a softgel, comprising an active material that would normally be unstable when stored within said dosage form, particularly when a standard gelatin material is used to make said dosage form.

BACKGROUND

Capsules are widely used in the pharmaceutical field as oral dosage form containers for administration to humans and animals of, e.g., pharmaceuticals, veterinary products, foods, and dietary supplements. Advantages of capsules over other dosage forms may include better patient compliance, greater flexibility in dosage form design, and less expensive manufacturing processes. Pharmaceutical capsules are conventionally divided into soft shell capsules (hereinafter softgel capsules) and hard shell capsules (hereinafter hard capsules). The characteristics of softgel and hard capsules are well known in the pharmaceutical field.

Hard capsule shells are generally manufactured using dip molding processes involving the use of pins dipped into solutions of the different ingredients that are needed for the making of the capsule shell containers. Methods for the manufacturing of soft gelatin or softgel capsule shells are also known in the art and are different from hard capsule shell manufacturing. Manufacturing of soft gelatin or softgel capsule shells at a production scale was introduced by Robert Pauli Scherer in 1933 with the invention of a rotary die encapsulation machine. The rotary die process involves continuous formation of a heat seal between two ribbons of gelatin simultaneous with dosing of the fill liquid into each capsule. Although manufacturing process speed and efficiency has improved with time, the basic manufacturing principle remains essentially unchanged. Before the encapsulation process takes place, two sub-processes are often carried out simultaneously, yielding the two components of a softgel capsule: (a) the gel mass which will provide the softgel capsule shell, and (b) the fill matrix for the softgel capsule contents. Softgel capsules have a continuous gelatin shell surrounding a liquid core, and are formed, filled, and sealed in one operation.

Softgel capsule walls are typically thicker than two-piece hard gelatin capsules, and their walls comprise plasticizers such as, for example, glycerol, sorbitol and/or propylene glycol to make the shell elastic. Processes for making softgel capsule shells are known, and softgel capsules are available commercially. See, e.g., Aulton, M., *Aulton's Pharmaceutics: The Design & Manufacture of Medicines*, 527-533 (Kevin M G Taylor, Ed., 3rd Ed., 2001). Softgel capsules have various advantages; they may show improved drug absorption, be easier to swallow, avoid dust handling issues, and have increased stability compared to other dosage forms. Softgel capsules may be filled with liquid fill such as oils and/or lipid soluble active ingredients such as pharmaceuticals, veterinary products, foods and dietary supplements.

Typical materials for both hard capsules and softgels include gelatin (of various sources including bovine, porcine, poultry, and/or fish) or non-gelatin materials such as synthetic polymers and/or plant-derived hydrocolloids. Gelatin is favorably used as shell forming material, particularly of softgels, due to its unique physiochemical properties, namely its oxygen impermeability and the combination of film-forming capability and thermoreversible sol/gel formation, that favor its use for the industrial capsule production, especially the softgel production via the rotary die process.

Softgel capsules may be desirable in view of their capability of storing liquid fills without requiring additional sealing procedures, as well as in some instances provide stability advantages when utilizing certain fills in view of the higher plasticizer content. The plasticizer content in softgels may further bring resistance to brittleness.

It may be desirable to provide stable dosage forms, made of a gelatin comprising material, and comprising active materials that would normally react with gelatin to provide instability and a change in the disintegration profile of the dosage form.

Typically, when faced with such stability issues, standard practice has been to focus the efforts on identifying suitable substitutes to gelatin, such as plant derived hydrocolloids (like in WO0137817) or synthetic polymers (like in WO9735537).

However, a need remains for achieving stable dosage forms using gelatin based materials.

SUMMARY

The instant disclosure relates to an innovative physically stable dosage form.

In a first aspect, the disclosure relates to a novel gelatin comprising dosage form article for oral administration and for containing therein a fill composition, the fill composition comprising one or more active materials capable of reacting with gelatin, and optionally one or more excipient materials, wherein the dosage form is made of a gelatin material and one or more plasticizers, the gelatin material having a mean molecular weight of less than about 130,000 g/mol and a low microgel content, wherein the fraction of microgel is of less than about 10% of the total number of gelatin chains of said gelatin material.

In a second aspect, the disclosure relates to a method of enhancing the physical stability of gelatin comprising dosage form articles.

In a third aspect, the disclosure relates to the use of the gelatin and plasticizer combination in dosage form articles for enhancing the physical stability thereof.

Surprisingly, the dosage form according to the present disclosure confers high physical stability and consistent disintegration profile over time.

DETAILED DESCRIPTION

Figure 1:
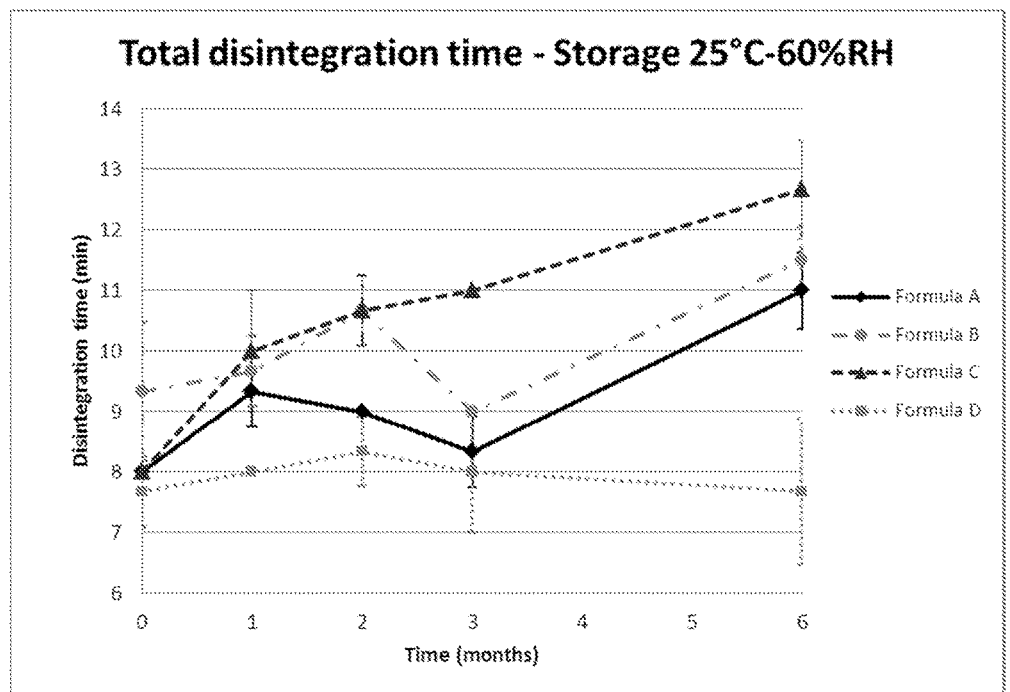
FIG. 1 is a graph showing total disintegration time after storage conditions at 25° C. and 60% relative humidity.

The term "physical stability or physically stable" as used herein means that the disintegration time is below 30 minutes after 3 months of storage and below about 45 minutes after 6 months of storage, at a temperature of about 40° C. and about 75% of relative humidity respectively, according to the test method herein.

The term "disintegration time" as used herein means the total time required for the dosage form to disintegrate according to the European Pharmacopeia 2.9.1.

The term "unmodified gelatin" or "standard gelatin" as used herein means standard pharmacopeial grade gelatin typically with mean molecular weight (Mw) greater than about 120,000 g/mol, typically at least about 130,000 g/mol, and/or with content of microgels (Molar mass greater than about 340,000 g/mol) of more than about 8%, typically at least about 10%, and/or fraction of small oligomers (Molar mass less than about 5,000 g/mol) of less than about 3%.

The term "microgel" as used herein means gelatin chains with molar mass greater than about 340,000 g/mol.

The term "oligomer" as used herein means gelatin chains having a molecular mass of less than about 70,000 g/mol.

Various embodiments will now be described to provide an overall understanding of the principles of the structure, function, manufacture, and use of dosage form articles and methods disclosed herein. One or more examples of these embodiments are illustrated in the accompanying figures. Those of ordinary skill in the art will immediately understand that features described or illustrated in connection with one example embodiment can be combined with the features of other example embodiments without generalization from the present disclosure.

In an embodiment, the disclosure contemplates a gelatin comprising dosage form article for oral administration and for containing therein a fill composition, the fill composition comprising one or more active materials capable of reacting with gelatin, and optionally one or more excipient materials, wherein the dosage form is made of a gelatin material and one or more plasticizers, the gelatin material having a mean molecular weight of less than about 130,000 g/mol, preferably less than about 120,000 g/mol, more preferably from about 100,000 g/mol to less than about 120,000 g/mol, even more preferably from about 100,000 g/mol to about 118,000 g/mol, and a low microgel content, wherein the microgel fraction of said gelatin material is of less than about 10%, preferably less than about 9%, preferably from about 0% to about 8%, more preferably from greater than about 5% to about 8%, of the total number of gelatin chains of said gelatin material.

Without wishing to be bound by theory, it is believed that the total content of microgels in the gelatin grade used directly impacts the ability of the final film generated to resist to chemical reactions with reactive fill active materials. Microgel contents above about 10%, have been found to result in higher instability particularly at storage in high relative humidity environments.

The gelatin material may comprise oligomers typically having a molecular weight of from greater than about 0 g/mol to less than about 70,000 g/mol. Typically, the fraction of oligomers in the gelatin material is greater than about 35%, preferably greater than about 45%, of the total number of gelatin chains of said gelatin material.

The content of oligomers having a molecular weight of less than about 25,000 g/mol may be contained at a fraction of greater than about 40%, preferably greater than about 45%, more preferably greater than about 47%, even more preferably from about 48% to about 60%, by number of the total number of oligomers chains present in the gelatin material.

In an embodiment, the fraction of small oligomers having a molecular weight of less than about 5,000 g/mol is greater than about 5%, preferably greater or equal to about 7%, even more preferably from about 7% to about 20%, most preferably from about 7% to about 15%, by number of the total number of oligomers chains present in the gelatin material.

Without wishing to be bound by theory, it is believed that small oligomers are more reactive with other gelatin chains and that the interaction of small oligomers with other gelatin chains will result in small or medium chains. This reduction of long chains which are insoluble in water will contribute to reducing physical instability. It is therefore desirable to increase the level of such small oligomers to leverage this effect.

An example of suitable gelatin material for use herein is Gelita® RXL from Gelita®.

Non-limiting examples of active ingredients for use herein include oils such as fish oil and krill oil. Most preferred active ingredients are selected from krill oil. Active ingredients herein are typically comprised at a level of from about 10% to about 100% by weight of the fill composition.

Excipients are typically selected from but not limited to the group consisting of lecithin, beeswax, glycerol monostearate, fumed silicon dioxide, water, oils such as vegetable oils like soybean oil, sunflower oil, flax seed oil, animal oils like fish oil, lecithins, sorbitan, emulsifying agents, glycols such as polyethyleneglycol (PEG) and propyleneglycol, and mixtures thereof. Excipients herein are typically comprised at a level of from about 0% to about 90% by weight of the fill composition.

Non-limiting examples of plasticizers for use in certain embodiments include polyethylene glycol, glycerol, sorbitol, sorbitan, mixtures of sorbitol and sorbitan such as polysorb, dioctyl-sodium sulfosuccinate, triethyl citrate (TEC), tributyl citrate, 1,2-propyleneglycol, mono-, di, or tri-acetates of glycerol, dibutyl sebecate, di- and triethyl phtalate, polyethylene glycol 6000, and mixtures thereof. Typically the plasticicers for use herein are selected from the group consisting of polyethylene glycol, glycerol, sorbitol, sorbitan, mixtures of sorbitol and sorbitan such as polysorb, and mixtures thereof, preferably from glycerol, sorbitol, polysorb, and mixtures thereof. In an embodiment the plasticizer consists of glycerol. At least one plasticizer may be used, or mixtures of more than one plasticizer, at about 10% to about 35% by weight, particularly about 20% by weight of the dosage form composition. Typically, the ratio of plasticizer to gelatinous material (plasticizer/gelatinous material) is from about 0.3 to about 1.0, preferably from about 0.35 to about 0.90, more preferably from about 0.4 to about 0.7.

Optionally, some embodiments comprise at least one additive selected from pigments, colorants, antifoam agents, antioxidants, waxes, and mixtures thereof.

Suitable pigments or colorants include pharmaceutically acceptable coloring agents, food acceptable colorants, or mixtures thereof. Examples of such colorants include, but are not limited to, azo-, quinophthalone-, triphenylmethane-, xanthene- or indigoid dyes; iron oxides or hydroxides; titanium dioxide; natural dyes; and mixtures thereof. Additional examples include patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, chlorophyllin, canthaxanthin, caramel, betanin and CANDURIN® pearlescent pigments. CANDURIN® is manufactured and marketed by Merck KGaA, Darmstadt, Germany and consists of titanium dioxide and/or iron oxide (approved food and pharmaceutical colorants in many countries) and potassium aluminum silicate as a color carrier.

In some embodiments, the optional colorants or mixtures thereof are present in an amount up to about 5% by weight, e.g., from about 0 to about 3% by weight, and from about 0 to about 2% by weight of the total weight of the composition.

Suitable antifoam agents include pharmaceutically acceptable antifoam agents, food acceptable antifoam agents, or mixtures thereof. Examples of such antifoam agents include, but are not limited to, silicone oils such as polydimethyl siloxane.

Suitable antioxidants are any compound or composition which is capable of counteracting the damaging effects of oxidation, including but not limited to enzymes and other substances, such as vitamin C, vitamin E, and beta carotene, butylated hydroxyanisole (BHA), butylated hydroxytoluene (BHT), propylgallate, ascorbyl palmitate, and mixtures thereof.

In certain embodiments, the instant disclosure is also directed to a method of enhancing the physical stability of a gelatin comprising dosage form for oral administration, comprising the step of providing a dosage form articles herein described.

In certain embodiments, the instant disclosure is also directed to use of a gelatin material and one or more plasticizers as described herein, to provide physical stability to a dosage form article for oral administration containing therein a fill composition comprising one or more active materials capable of reacting with gelatin, and optionally one or more excipient materials.

The compositions and methods of the present disclosure are useful for, but not limited to, for example, oral administration of at least one of pharmaceuticals, veterinary products, foods, and dietary supplements to humans or animals.

Measurements on average molecular weight, microgel content, and oligomer content are carried out following the following procedure. Molecular weight distribution is measured by HPLC (Waters e2695 Separations module with UV/Visible detector with data analysis system Astra software version 5.3.4): gelatins are dissolved in SDS buffer and injected. Analysis is performed using UV detector at 214 nm.

Examples

Table 1 gives examples of the compositions in weight percentages of softgel dosage form compositions (by weight of the dosage form) as well as exemplary fills in weight percentages (by weight of fill).

TABLE 1

| | | A | B | C | D | E | F | G |
|---|---|---|---|---|---|---|---|---|
| Softgel dosage form composition | Gelatin | | | | | | | |
| | Bovine bone[1] | 45 | 45 | 45 | — | — | — | — |
| | Bovine bone[2] | — | — | — | 45 | 39 | 46 | 45 |
| | Plasticizer | | | | | | | |
| | Glycerol[3] | 23 | 9 | 9 | 23 | 26 | 4 | 21 |
| | Sorbitol (70% active)[4] | — | — | 10 | — | — | 6 | — |
| | Mix of sorbitol and sorbitan[5] | — | 9 | — | — | — | 9 | — |
| | Minors and Water | Balance | Balance | Balance | Balance | Balance | Balance | Balance |
| Fill composition | Active ingredient | | | | | | | |
| | Krill Oil[6] | 100 | 100 | 100 | 100 | 100 | 80 | 60 |
| | Excipient | | | | | | | |
| | Polyoxyethylene sorbitan monooleate[7] | — | — | — | — | — | 20 | — |
| | Fish oil[8] | | | | | | | 40 |

[1]Bovine bone manufactured by PB Gelatins grade Limed bovine bone gelatin B165 (microgel content of about 13%)
[2]Gelita ® RXL manufactured and sold by Gelita ® (microgel content of about 7%)
[3]Glycerol from Cooper
[4]Sorbitol non cristallisable 70% from Roquette
[5]Mix of sorbitol and sorbitan Polysorb 85/70 from Roquette
[6]Krill oil Superba Krill oil TM from Aker Biomarine
[7]Polyoxyethylene sorbitan monooleate Radiamuls Sorb 2157K from Oleon
[8]Fish oil 18/12 TG from Polaris Preparation of the Softgel:

Plasticizers are weighed and mixed at 80° C. and homogenized under mechanical stirring. When the solution is homogeneous, the weighed gelatin is added and homogenized under mechanical stirring until a temperature of 80° C. is attained. Mechanical stirring is maintained until the gelatin is melted. The gelatin mass is then put under vacuum for removal of air bubbles under low mechanical stirring at 80° C. The gelatin mass is then finally put at 60° C. under low mechanical stirring.

Gelatin viscosity is measured with a viscosimeter (such as Brookfield LVDII+) and viscosity is adjusted with addition of water to obtain a viscosity of 16,000 cps+/−4000 cps at 60° C. The gelatin mass is finally transferred into the soft gelatin machine.

Softgel capsules 10 oval filled with fill weight of 500 mg±5% are produced with a softgel machine (Bochang machine).

Softgel capsules produced and dried are finally stored in polypropylene bottles for the stability study at different humidity conditions: 25° C./60% RH, 30° C./65% RH and 40° C./75% RH.

Figure 2:
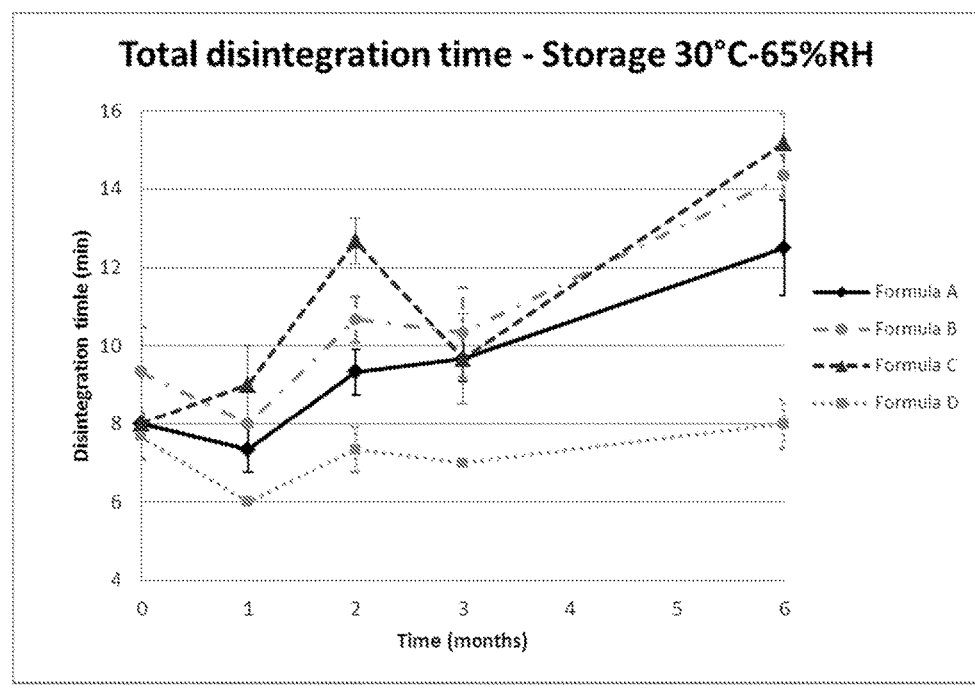
FIG. 2 is a graph showing total disintegration time after storage conditions at 30° C. and 65% relative humidity.
Figure 3:
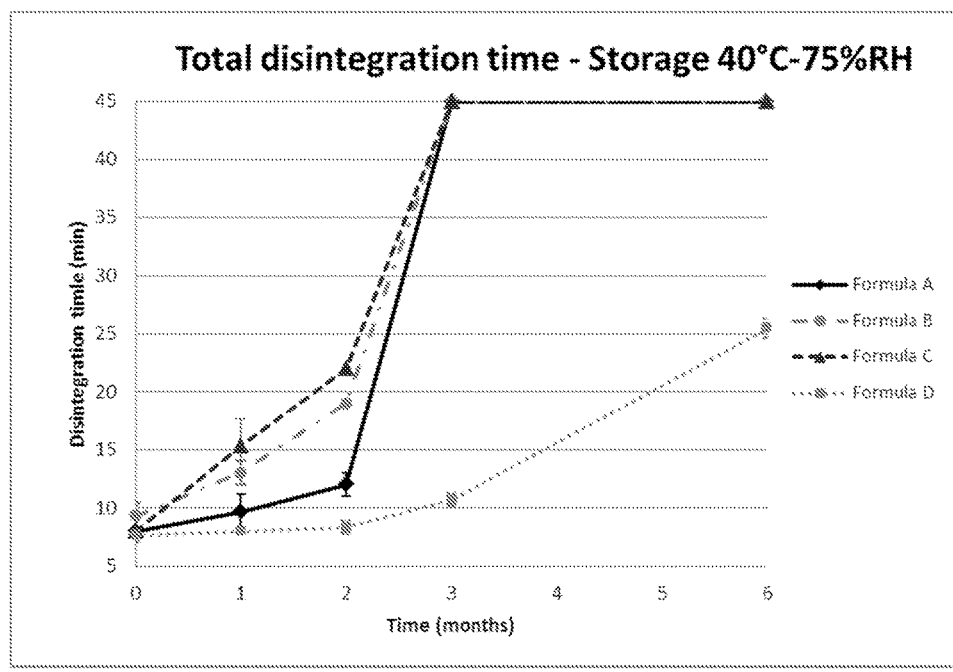
FIG. 3 is a graph showing total disintegration time after storage conditions at 40° C. and 75% relative humidity.

A disintegration test is used to evaluate the physical stability of the dosage form articles of Examples A to D, the results of which are illustrated in FIG. 1 to FIG. 3.

Disintegration tests are performed according to EP 2.9.1. This test is aimed at determining whether capsules disintegrate within the prescribed time when placed in water at 37° C. Disintegration equipment such as Sotax DT2 could be used. One capsule is placed in each tube using the 2 basket-rack. Complete disintegration of capsules is evaluated and recorded, tests are stopped after 45 minutes even if capsules are not totally disintegrated.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What we claim is:

1. A gelatin-comprising dosage form article for oral administration and containing therein a fill composition, the fill composition comprising one or more active materials capable of reacting with gelatin, and optionally one or more excipient materials, said active material comprising krill oil, wherein the dosage form is made of a gelatin material and one or more plasticizers, the gelatin material having a mean molecular weight of less than about 130,000 g/mol, a low microgel content, and a small oligomer content, wherein the fraction of microgel, having gelatin chains with molar mass greater than 340,000 g/mol, is of about 10% or less of the total number of gelatin chains of said gelatin material and wherein the fraction of small oligomers having a molecular weight of about 5,000 or less is about 5% or greater by number of the total number of oligomers present in the gelatin material, and wherein the plasticizer consists essentially of glycerol.

2. The dosage form article according to claim 1, wherein the mean molecular weight is about 120,000 g/mol or less.

3. The dosage form article according to claim 1, wherein the microgel fraction is of about 9% or less of the total number of gelatin chains of said gelatin material.

4. The dosage form article according to claim 1, wherein the dosage form article is a softgel dosage form.

5. The dosage form article according to claim 1, wherein the active material consists of krill oil.

6. The dosage form article according to claim 1, wherein the ratio of plasticizer to gelatin material (plasticizer/gelatin material) is from about 0.3 to about 1.0.

7. The dosage form article according to claim 1, wherein the dosage form is stable, in that the disintegration time is below about 30 minutes after about 3 months of storage and below about 45 minutes after about 6 months of storage, at a temperature of about 40° C. and about 75% of relative humidity respectively.

8. The dosage form article according to claim 1, wherein the excipient material is selected from the group consisting of lecithin, beeswax, glycerol monostearate, fumed silicon dioxide, water, vegetable oils, animal oils, sorbitan, emulsifying agents, glycols, and mixtures thereof.

9. A method of enhancing the physical stability of a gelatin comprising dosage form for oral administration, comprising providing a dosage form article according to claim 1.

* * * * *